United States Patent
Ochs

Patent Number: 5,830,495
Date of Patent: Nov. 3, 1998

[54] DENTAL FLOSS WITH INCREASED LOADING WEIGHT

[76] Inventor: Harold D. Ochs, 83 Clover Hill Rd., Flemington, N.J. 08822

[21] Appl. No.: 676,881

[22] Filed: Jul. 3, 1996

[51] Int. Cl.⁶ ............................. A61K 9/70; A61F 13/00
[52] U.S. Cl. ........................................... 424/443; 424/401
[58] Field of Search ................................. 424/401, 443; 427/49, 2, 175

[56] References Cited

U.S. PATENT DOCUMENTS

| | | | |
|---|---|---|---|
| 4,911,927 | 3/1990 | Hill et al. | 424/443 |
| 5,503,842 | 4/1996 | Fazan et al. | 424/443 |

*Primary Examiner*—Thurman K. Page
*Assistant Examiner*—Kathryne E. Shelborne

[57] ABSTRACT

A dental floss product and a method for making the same. A texturized dental floss substrate having a plurality of strands is provided. Each of the strands is formed from a plurality of individual filaments. At least one of the strands in the substrate contains filaments which were curled, looped, twisted, bent or crimped prior to their incorporation into a strand. The texturized dental floss substrate has an indefinite length, a cross-section perpendicular to the length, an exterior surface, and a depth defined as the distance from the exterior surface toward the center of the cross-section. The texturized dental floss substrate also has a substrate weight and an overcoating applied to the exterior surface. The overcoating is formed of a carrier and at least one adjuvant, and has a weight which exceeds 10% of the substrate weight. The concentration of the overcoating decreases in a direction from the outer surface of the floss toward the interior, i.e., the concentration of the overcoating is greater at the exterior of the coated floss and lesser in the interior region thereof.

22 Claims, 5 Drawing Sheets

DENTAL FLOSS WITH INCREASED LOADING WEIGHT

FIELD OF THE INVENTION

The present invention relates generally to oral hygiene. More specifically, the present invention relates to an improved dental floss product which has been loaded around its exterior surface with an increased quantity of a coating material.

BACKGROUND OF THE INVENTION

Dental floss is typically formed from a nylon multifilament material substrate coated with various substances and adjuvants. The weight of the floss coating (also referred to as the floss loading) typically does not exceed 55% of the substrate weight. For example, the mint waxed dental floss product currently sold by Johnson & Johnson has a coating consisting of microcrystalline wax and mint flavor powder, the combination of which equals 35% of the weight of the multi-filament substrate. Similarly, the waxed baking soda dental floss product and the waxed fluoride dental floss product currently sold by Johnson and Johnson have loadings which equal 54% and 40%, respectively, of the base floss weight.

It is desirable to maximize the percentage of dental floss loading because, among other things, increased loading generally allows more adjuvants such as fluoride, baking soda, or flavorings to be delivered with the dental floss product, thereby giving the product greater consumer appeal. Until recently, it was believed that, if the dental floss loading began to exceed about 50–55% of the base floss weight, the dental floss would become undesirable from a user standpoint, be unmanufacturable and have dispensability problems. U.S. Pat. Nos. 5,098,711 and 5,165,913, both to Hill et al., disclose dental flosses comprising a plurality of strands of, e.g., nylon, each of said strands comprising a plurality of individual nylon monofilaments. The Hill et al. patents taught that satisfactory dental flosses could be manufactured having loadings up to 100% of the substrate weight. These patents to Hill et al. taught that the floss loading weight could be extended beyond previous limits by positioning a cleaning preparation throughout the interior of the floss. More particularly, the patents to Hill et al. taught the deposition of a cleaning preparation in spaces between the several strands and between the individual filaments comprising each strand. The cleaning preparation activates as the floss splays upon being pulled between the teeth, thereby delivering the cleaning preparation to the oral cavity, especially the surfaces of the teeth. The manufacture of the Hill et al. floss is complicated by the requirement that the several strands and the individual filaments in the strands be drawn apart and/or separated at the time that the cleaning preparation is being loaded into the floss.

It is an object of the present invention to provide a floss with an increased loading percentage which approaches or even exceeds the loading percentages taught by the Hill et al. patents.

It is a still further object of the present invention to provide a coating which can be easily loaded onto a floss substrate, but which does not necessarily require the individual filaments and strands in the floss to be drawn apart and/or separated at the time that the floss is loaded.

These and other objects and advantages of the invention will become more fully apparent from the description and claims which follow or may be learned by the practice of the invention.

SUMMARY OF THE INVENTION

The present invention is directed to a dental floss product and a method for making the same. A texturized dental floss substrate having a plurality of strands is provided. Each of the strands is formed from a plurality of individual filaments. At least one of the strands in the substrate contains filaments which were curled, looped, twisted, bent or crimped prior to their incorporation into a strand. The texturized dental floss substrate has an indefinite length, a cross-section perpendicular to the length, an exterior surface, and a depth defined as the distance from the exterior surface toward the center of the cross-section. The texturized dental floss substrate also has a substrate weight and an overcoating applied to the exterior surface. The overcoating is formed of a carrier and at least one adjuvant, and has a weight which exceeds 10% of the substrate weight. The concentration of the overcoating decreases in a direction from the outer surface of the floss toward the interior, i.e., the concentration of the overcoating is greater at the exterior of the coated floss and lesser in the interior region thereof.

In order that the manner in which the above-recited and other advantages and objects of the invention can be understood and appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DESCRIPTION OF PREFERRED EMBODIMENTS

Figure 1:
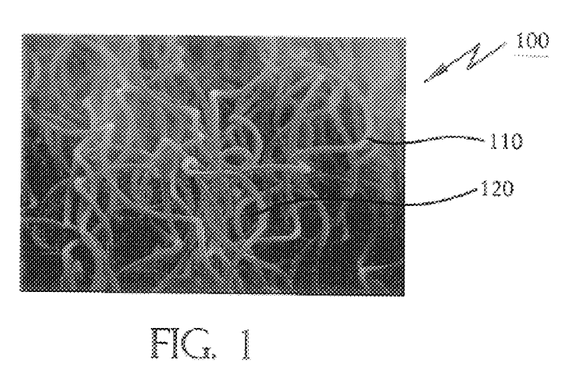
FIG. 1 is a scanning electron micrograph (SEM) showing at 100 times magnification a side view of a texturized dental floss substrate used for forming an improved dental floss product having an increased loading weight, in accordance with a preferred embodiment of the present invention.
Figure 2:
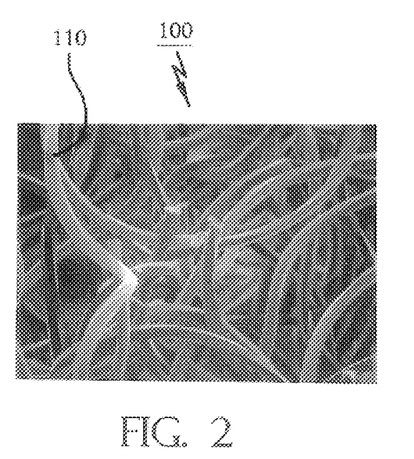
FIG. 2 is an SEM showing at 250 times magnification a cross-sectional view of the texturized dental floss substrate shown in FIG. 1.
Figure 3:
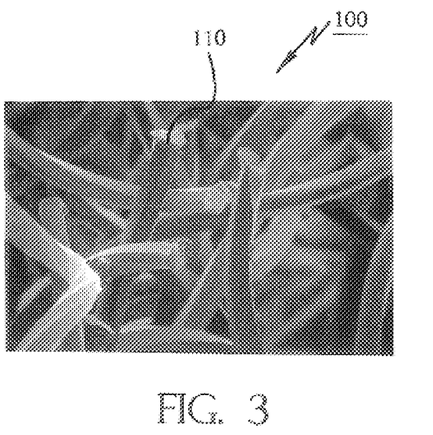
FIG. 3 is an SEM showing at 500 times magnification a further cross-sectional view of the texturized dental floss substrate shown in FIG. 1.

Referring now to FIG. 1, there is shown an SEM illustrating a side view of a texturized dental floss substrate 100 used for forming an improved dental floss product having an increased loading weight. Texturized dental floss substrate 100 is formed of a plurality of strands. Each such strand is made of a plurality of individual filaments (or monofilaments) 110. Monofilaments 110 may be formed from polymers such as nylon 6 and 66, rayon, polyester, acetate polymers, polyolefins such as polypropylene, as well as cotton, wool and other staple yarns. Typically, monofilaments 110 have denier ranging from about 0.5 to about 6.0. "Denier" is the weight in grams of 9000 meters of material. Hence, a monofilament which is 9000 meters long and weighs one gram is a "1-denier" monofilament. Similarly, a strand (which, as mentioned above, comprises a plurality of monofilaments) which is 9000 meters long and weighs one hundred grams is a "100-denier" strand. The number of strands comprising floss substrate 100 will vary depending, e.g., on the denier which is desired for the floss substrate, the number of monofilaments per strand, and the denier of the individual monofilaments. For example, if it is desired to provide a floss substrate 100 having a denier of 1200, the floss substrate might consist of a dozen (12) strands wherein each strand consists of one hundred monofilaments 110 each having a denier of 1. Alternatively, e.g., a 1200 denier floss substrate could as well consist of eight strands, each of said strands consisting of seventy-five monofilaments 110 each having a denier of 2. Other such combinations useful for dental floss substrates will be readily apparent to those skilled in the art. If desired, some or all of the filaments 110 can be colored utilizing any dye such as FD&C Green No. 3, FD&C Red No. 40 or mixtures of these or other similar dyes.

Prior to combining individual filaments 110 into a strand, at least some, and preferably all of the individual filaments 110 are subjected to a "texturizing" process which imparts curls, loops, twists, bends, crimps and turns to the filaments 110. The filaments 110 are texturized by disturbing the surface of the individual filaments to enable the filaments to better hold coatings loaded thereon. The preferred texturized filaments 110 have a permanent curl, loop, twist, bend, crimp or turn. Several texturization processes which disturb the filament surface can be used to form texturized filaments 110. For example, individual filaments 110 may be texturized by moving such filaments past an air nozzle which aims hot air at the filaments, or by curling the filaments under heat and then releasing the filaments. Suitable systems and methods for texturizing yarns or filaments are disclosed in Carrol-Porczynski, Charles Z., "Manual of Man-Made Fibers, Their Manufacture, Properties, and Identification," Chemical Publishing Co., Inc., New York, N.Y., 1961 at pp. 160–171, and Linton, George E., "The Modem Textile and Apparel Dictionary," 4th Ed., 1973, at pp. 588–592, the disclosure of both of which are hereby incorporated herein by reference.

After some or all of filaments 110 have been texturized, a plurality of filaments 110 are combined together to form a "texturized" strand. Such a strand is referred to as being texturized because, among other things, the curls, loops, twists, bends, crimps and turns previously imparted to the filaments 110 cause the creation of gaps or voids 120 in substrate 100. As explained more fully below, these gaps or voids 120 provide sites for holding coatings to be applied to the floss substrate. In a preferred embodiment of the present invention, each texturized strand contains about 100 to 800 individual filaments 110.

Once the texturized strands have been formed as described above, the texturized floss substrate 100 is formed by combining together a plurality of texturized strands. The preferred means of combining the strands is by twisting them together or by air tacking adjacent strands. Such twisting of the strands results in a texturized floss substrate 100 that is more resistant to shredding and filament separation than would otherwise be achieved. However, texturized floss substrate 100 can be made with little or no twist or it can be braided as in a dental tape. The twist can be from 0.0 to 6.0 turns per inch, with a preferred twist of 1.0 to 2.0 turns per inch. In a preferred embodiment of the present invention, texturized dental floss substrate 100 contains about 2 to 12 individual strands, each of said strands having a denier ranging from about 50 to 300, the preferred floss substrate denier ranging as mentioned below from about 500–1600.

The tensile strength of the texturized dental floss substrate 100 is preferably between 5 and 25 pounds, although higher tensile strengths are acceptable. The preferred tensile strength is about 7 to 15 pounds. A floss substrate having a tensile strength of less than 5 pounds will tend to break easily during use and would be unacceptable for dental floss, and a substrate having a tensile strength of more than 25 pounds offers no advantages but is less economical to manufacture. The texturized dental floss substrate 100 may be 200–2000 However, a texturized dental floss substrate of 500–1600 denier is preferred so as to provide a proper hand feel for the dental floss.

Figure 4:
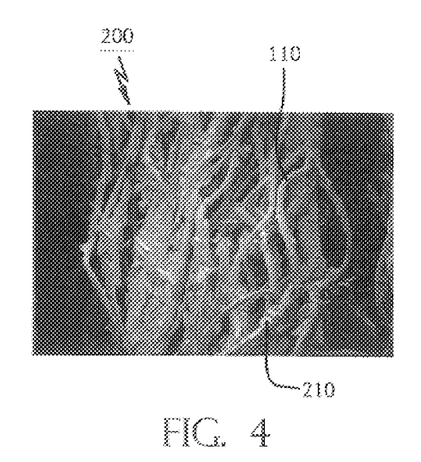
FIG. 4 is an SEM showing at 100 times magnification a side view of a texturized dental floss substrate which has been uniformly loaded throughout its cross-section with a cleaning preparation.
Figure 5:
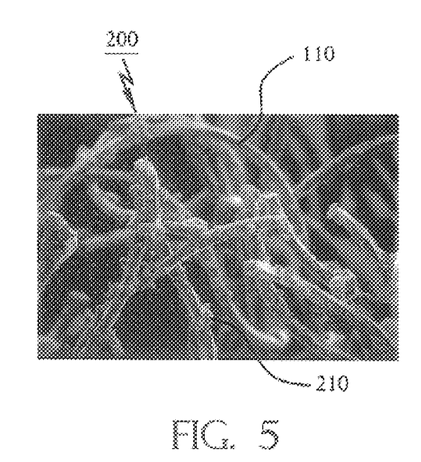
FIG. 5 is an SEM showing at 250 times magnification a cross-sectional view of the dental floss substrate shown in FIG. 4.
Figure 6:
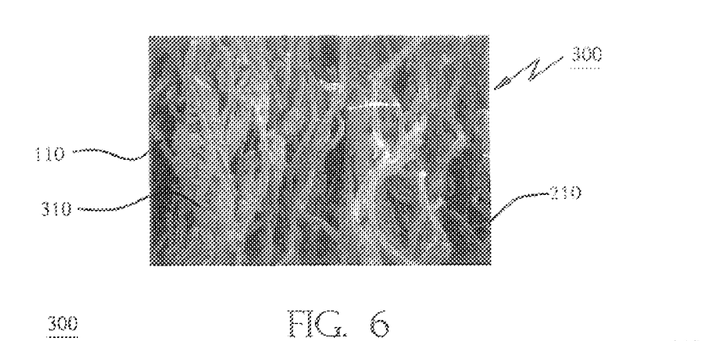
FIG. 6 is an SEM showing at 100 times magnification a side view of a texturized dental floss substrate which has been uniformly loaded throughout its cross-section with a cleaning preparation and then overcoated about its exterior with an overcoating composition, in accordance with a preferred embodiment of the present invention.
Figure 7:
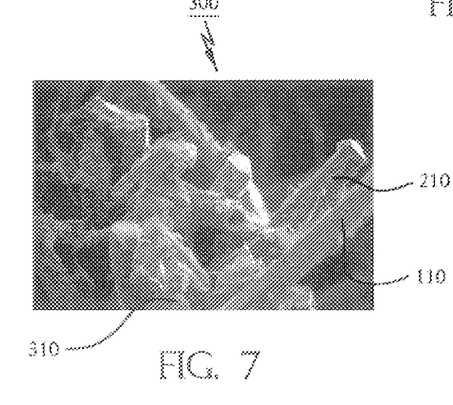
FIG. 7 is an SEM showing at 500 times magnification a cross-sectional view of the texturized dental floss product shown in FIG. 6.
Figure 8:
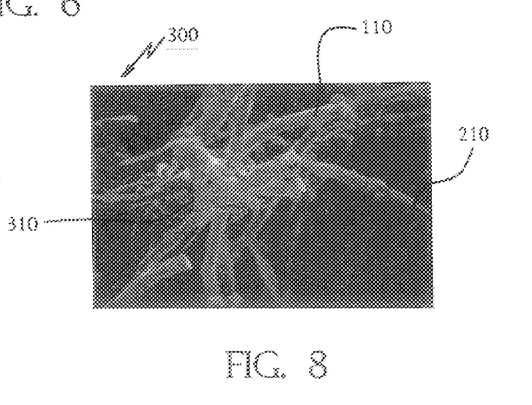
FIG. 8 is an SEM showing at 250 times magnification a further cross-sectional view of the dental floss product shown in FIG. 6.

After the texturized dental floss substrate 100 has been formed as described above, this texturized substrate is used to manufacture the improved dental floss product with increased loading which is the subject of the present application. As described below, the manufacturing process of the present invention is performed in two steps. In the first step, a cleaning preparation is loaded uniformly throughout the cross-section of substrate 100 by depositing the cleaning preparation with a uniform concentration in the voids 120 throughout the cross-section of substrate 100. This first manufacturing step results in an "intermediate floss" 200 which is shown in FIGS. 4 and 5. In the second manufacturing step, an overcoating is applied to the exterior surface of the intermediate floss 200. In contrast to the cleaning preparation, this overcoating is distributed primarily around the exterior surface of the intermediate floss, and the concentration of the overcoating material on the floss substrate decreases as the distance from the exterior surface of the floss substrate toward the longitudinal centerline of the floss substrate increases. This second manufacturing step results in a final floss product 300 which is shown in FIGS. 6–8.

Manufacture of the Intermediate Floss

The step of manufacturing the intermediate floss from texturized substrate 100 is described in U.S. Pat. No. 4,911,927 to Hill et al., at col. 25, line 52 through col. 27, line 37, which patent is incorporated herein in its entirety by reference. The process for making the intermediate floss consists of spreading the texturized filaments 110 in texturized substrate 100, loading a cleaning preparation in a molten state between the spread floss filaments 110, and then reforming the spread filaments back to their initial positions. During the loading step, sufficient mechanical and hydraulic pressure is applied to the substrate at the point of contact with the cleaning preparation to ensure that between 10 and 100 mg of the preparation is loaded into each yard of the texturized substrate 100. Suitable cleaning preparations for use in manufacturing the intermediate floss are described in U.S. Pat. Nos. 5,165,913 and 4,911,927 to Hill et al. In a preferred embodiment of the present invention, the cleaning preparation carried by the intermediate floss has a weight equal to 5% to 120% of the weight of the texturized substrate 100.

Referring now to FIGS. 4 and 5, there are shown side and cross-sectional views, respectively, of the intermediate floss 200 formed in accordance with the process described above. As shown more clearly in FIG. 5, the cleaning preparation (indicated by reference numeral 210) has a relatively uniform concentration throughout the cross-section of the intermediate floss 200.

Application of an Overcoat to the Intermediate Floss

The second step in the manufacture of the dental floss product of the present invention consists of applying an overcoat to the intermediate floss 200. One purpose of the overcoat is to provide oral care adjuvants, such as, additional cleaning agents, flavors, antimicrobials, decay preventive materials, and the like, to intermediate floss 200. The overcoat also functions to "lock" the aforementioned cleaning preparation into the floss substrate prior to use of the final floss product.

The overcoat comprises at least one carrier material and at least one adjuvant useful for inclusion in oral care products such as dental floss. Carriers which are useful include paraffin wax, microcrystalline wax (MCW), beeswax, polyvinyl alcohol, hydroxypropyl cellulose, water-soluble polyethylene glycol (PEG) polymers, nylon polymers, ethylene-vinyl acetate copolymers, and the like. Additional polymers which are useful as carriers are set forth hereinafter. Adjuvants which are useful include fluoride compounds such as sodium fluoride, stannous fluoride, and sodium mono-fluorophosphate; anti-microbials such as cetyl pyridinium chloride (CPC), sodium bicarbonate; tetrasodium pyrophosphate; peroxides such as calcium peroxide and sodium percarbonate; nitrates such as potassium nitrate and strontium nitrate; flavorants; flavor enhancers; colorants; antibiotics; plaque inhibitors; polishing agents; fillers; buffering agents, and the like. During manufacture, the carrier is melted and thoroughly mixed with one or more of the adjuvants. The molten mixture is then applied to the intermediate floss with the majority of the overcoating remaining on the outer surface of the floss, where it can be readily released upon use.

The preferred amount of overcoat which is applied to the exterior surface of intermediate floss 200 varies based on the weight of cleaning preparation which has been loaded into the intermediate floss 200. A particular preferred cleaning preparation used for the present invention is comprised of the following by weight: 67.4% surfactant (poloxamer 407), 10.0% coating (silicone 1500 AF), 15.0% dicalcium phosphate, 0.2% EDTA, 0.1% propylgallate, 2.3% insoluble saccharin and 5.0% herb mint flavor. In a first preferred example of the present invention, the aforementioned preferred cleaning preparation is used to form the intermediate floss, and an overcoat comprised of 98% water-soluble PEG 1450 and 2% fluoride is used to form the final dental floss product; in a second preferred example of the present invention, the aforementioned preferred cleaning preparation is used to form the intermediate floss, and an overcoat comprised of 75% water-soluble PEG 1450 and 25% baking soda is used to form the final dental floss product. In the two preferred examples mentioned immediately above, the weight of the cleaning preparation carried by the dental floss substrate is about 50% of the weight of the base texturized floss substrate 100, and the weight of the overcoating is about 100% of the weight of the base texturized substrate 100. In accordance with further embodiments, set forth in Table I below are preferred overcoat weight ranges corresponding to several different intermediate floss loading levels. All the weights expressed in Table I below are relative weights that are expressed as a percentage of the weight of the texturized substrate 100 used to form the intermediate floss.

TABLE I

| Weight of Cleaning Preparation in Intermediate Floss | Range of Overcoating Weight Applied to the Exterior Surface of Intermediate Floss |
| --- | --- |
| 10% | 30–100% |
| 20% | 25–95% |
| 30% | 25–90% |
| 40% | 20–85% |
| 50% | 20–85% |
| 60% | 15–80% |
| 70% | 15–75% |
| 80% | 10–70% |
| 90% | 10–65% |
| 100% | 10–60% |
| 110% | 10–60% |
| 120% | 10–60% |

The polymeric carrier used to form the overcoat must have good adhesion to the intermediate floss 200 and must be non-toxic. Further, it is desirable that the polymeric material used to form the overcoat be a film former so that a uniform continuous coating can be achieved along the exterior surface of the intermediate floss. It is further desirable that the polymeric carrier be capable of being hydrated by the aqueous-based fluids found in the oral cavity so as to allow for rapid release of the adjuvants in the overcoating. Finally, the polymeric overcoating is preferably clear, so as to allow dyes applied to monofilaments 110 to be visible, and sufficiently abrasion-resistant to resist cracking or flaking which may result in undesirable loss of adjuvants during the latter stages of manufacture or handling prior to placement of the final dental floss product in the oral cavity.

Specific polymeric carriers which are useful for the overcoat in the present invention include: alkyl monester of poly(methyl vinyl ether/maleic acid); polyvinyl pyrrolidones; acrylamide/acrylate/butylaminoethyl methacrylate polymers (polymers of this type are sold by National Starch & Chemical Corporation under the trademark "Amphomer"); vinyl acetate/crotonic acid/vinyl neodecanoate terpolymers (terpolymerics of this type of sold by the National Starch & Chemical Corporation under the trademark "Resyn 28-2930"); vinyl acetate/crotonic acid copolymers (copolymers of this type are sold by the National Starch & Chemical Corporation under the trademark "Resyn 28-1310"); and terpolyamides comprised of the copolymerization products of three polyamide precursors, a dicarboxylic acid-diamine reaction product, a second but dissimilar dicarboxylic acid-diamine reaction product, and a latam (terpolymers of this type are sold by Belding Chemical Industries as BCI 600 series nylon.)

Referring now to FIGS. 6–8, there are shown side and cross-sectional views of the overcoated floss 300 formed in accordance with the process described above. As shown more clearly in FIGS. 7–8, the overcoat (indicated by numeral 310) has its greatest concentration at the exterior surface of floss 300, and the concentration of material 310 decreases as the distance from the exterior surface toward the longitudinal centerline of the floss increases.

Figure 9:
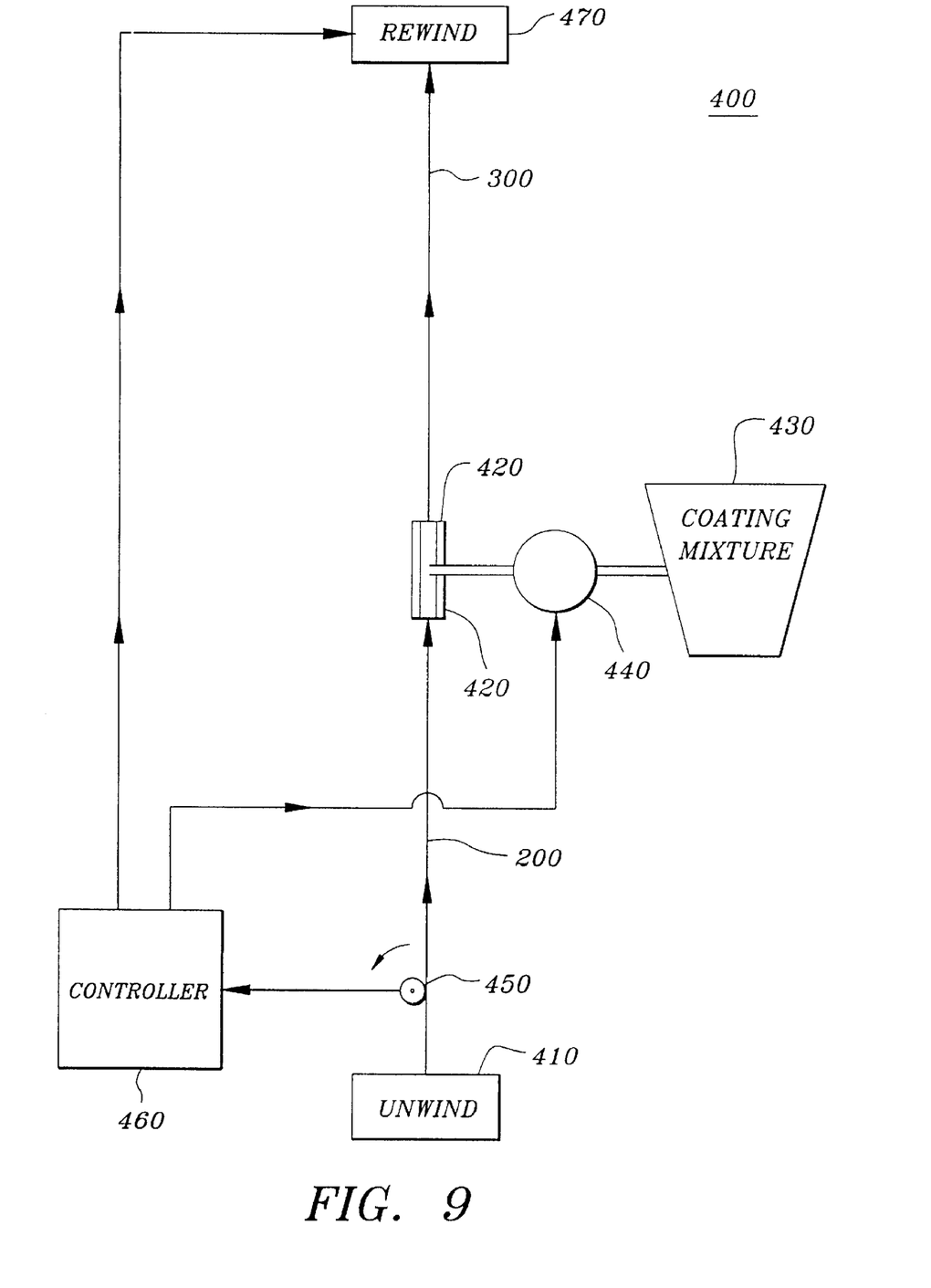
FIG. 9 shows a system for applying an overcoating to an exterior surface of a dental floss substrate, in accordance with a preferred embodiment of the present invention.

Referring now to FIG. 9, there is shown in block diagram form a system 400 for applying an overcoating to the exterior surface of intermediate floss 200, in accordance with a preferred embodiment of the present invention. A roll of intermediate floss 200 is unwound at unwinding station 410. The intermediate floss 200 is then passed through a die station 420 where the overcoating material described above is applied uniformly and continuously to the exterior surface of the intermediate floss 200. Die station 420 includes a groove (not shown) through which the intermediate floss 200 passes. An opening (also not shown) is provided at the base of the groove for delivering the coating material in a molten state into the base of the groove. The opening in die station 420 is coupled to a heated supply tank 430 by a coating pump 440. Heated supply tank 430 maintains the coating mixture contained therein in a molten state. As the overcoated floss exits die station 420, the molten overcoating cools and solidifies and the finished floss 300 is then rewound onto a supply roll at a rewind station 470.

A velocity sensor 450 is provided for monitoring the velocity of floss passing through system 400. The output of velocity sensor 450 is coupled to a controller 460. Controller 460 is also coupled to and provides control signals to pump 440 and to rewind station 470. The control signal provided to pump 440 ensures that, for a given length of intermediate floss 200 passing through die station 420, a constant and controlled amount of molten coating material is always delivered to die station 420 and applied uniformly along the given length of floss. The control signal provided to rewind station 470 is provided to ensure that finished floss 300 is wound onto an output roll at the same rate that intermediate floss 200 is unwound at station 410. Finally, a tensioner (also not shown) is provided for maintaining a tension of about 10–150 g in the floss as it moves from unwind station 410 to rewind station 470.

Figure 10:
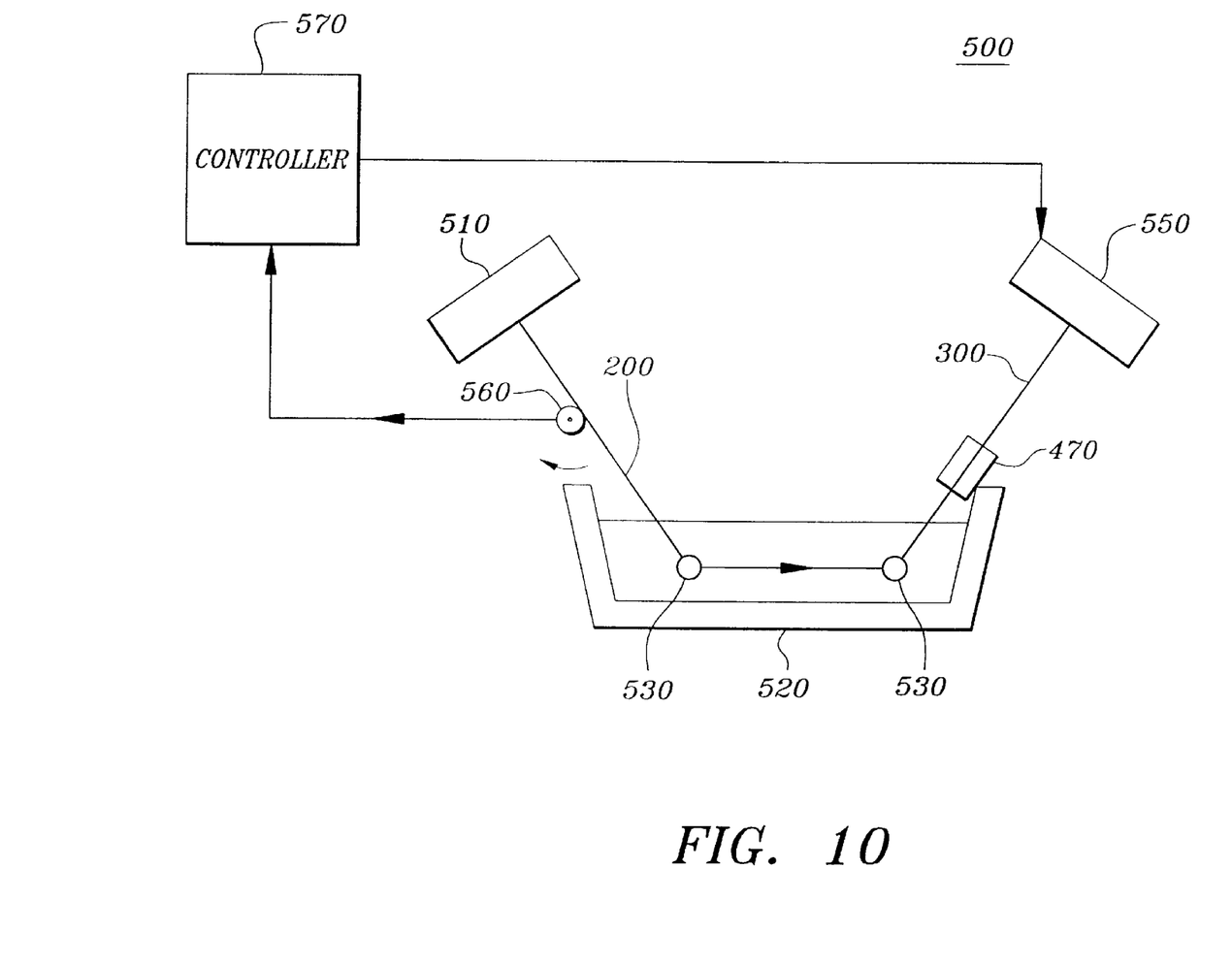
FIG. 10 shows a system for applying an overcoating to an exterior surface of a dental floss substrate, in accordance with an alternative preferred embodiment of the present invention.

Referring now to FIG. 10, there is shown in block diagram form a system 500 for applying an overcoating to the exterior surface an intermediate floss 200, in accordance with an alternative preferred embodiment of the present invention. A roll of intermediate floss 200 is unwound at unwinding station 510. The intermediate floss 200 is then passed through a heated tank 520 where the overcoating material described above is applied uniformly and continuously in molten form to the exterior surface of the intermediate floss 200. Heated supply tank 520 maintains the coating mixture contained therein in a molten state. Eyelet guides 530 are provided for guiding and directing the floss through tank 520. A die 540 is provided for removing excess molten coating material from the floss exiting tank 520. As the overcoated floss exits heated supply tank 520 and passes through die 540, the molten overcoating cools and solidifies, and the finished floss 300 is then rewound onto a supply roll at a rewind station 550.

A velocity sensor 560 is provided for monitoring the velocity of floss passing through system 500. The output of velocity sensor 560 is coupled to a controller 570. Controller 570 is also coupled to and provides a control signal to rewind station 550. The control signal provided to rewind station 550 is provided to ensure that finished floss 300 is wound onto an output roll at the same rate that intermediate floss 200 is unwound at station 510. Finally, a tensioner (also not shown) is provided for maintaining a tension of about 10–150 g in the floss as it moves from unwind station 510 to rewind station 550.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. A method for forming a dental floss product, comprising the steps of:
   (A) forming a plurality of texturized filaments;
   (B) forming a texturized dental floss substrate from said texturized filaments, said texturized dental floss substrate being formed of a plurality of strands each of which is formed from a plurality of individual filaments and wherein at least one of said strands contains ones of said texturized filaments, said texturized dental floss substrate having a length, a cross-section perpendicular to said length, an exterior surface, a depth defined as a distance from said exterior surface toward a center of said cross-section, and a substrate weight; and
   (C) after step (B), forming said dental floss product by applying an overcoating to said exterior surface of said texturized dental floss substrate, said overcoating being formed of a carrier and at least one adjuvant;
   wherein said overcoating has a weight which exceeds 10% of said substrate weight, and wherein said overcoating has a concentration which decreases as said depth increases.

2. The method of claim 1, said texturized dental floss substrate having an internal region distinct from and bounded by said exterior surface, further comprising the step of:
   (D) prior to step (C), depositing a cleaning preparation in spaces between filaments positioned within said internal region, said cleaning preparation have a weight equal to 5% to 120% of said substrate weight.

3. The method of claim 2, wherein said dental floss product has a total loading weight representing the combination of said weight of said overcoating and said weight of said cleaning preparation, wherein said total loading weight is at least 40 percent of said substrate weight.

4. The method of claim 2, wherein said at least one of said strands is formed by combining one of said texturized filaments with at least one untexturized filament.

5. The method of claim 2, wherein said at least one of said strands is formed by combining only ones of said texturized filaments.

6. The method of claim 2, wherein said texturized dental floss substrate contains from two to twelve of said strands, and wherein each of said strands contains from 100 to 800 of said individual filaments.

7. The method of claim 2, wherein said carrier is formed of an overcoat wax, wherein said overcoat wax is selected from the group consisting of soluble polyethylene glycol, microcrystalline wax, beeswax and paraffin wax, and wherein said at least one adjuvant is selected from the group consisting of fluoride compounds, anti-microbials, tetrasodium pyrophosphate, peroxides, nitrates, flavorants, flavor enhancers, colorants, antibiotics, plaque inhibitors, polishing agents, fillers and buffering agents.

8. The method of claim 1, wherein said step of applying said overcoating to said exterior surface of said dental floss substrate comprises the step of pulling said dental floss substrate over a die having a cavity containing a molten overcoating mixture, and then allowing said molten overcoating mixture on said texturized exterior surface to cool.

9. The method of claim 1, wherein said step of applying said overcoating to said texturized exterior surface of said dental floss substrate comprises the step of pulling said dental floss substrate through a bath containing a molten overcoating mixture, and then allowing said molten overcoating mixture on said texturized exterior surface to cool.

10. A dental floss product, comprising: a texturized dental floss substrate formed from texturized filaments, said texturized dental floss substrate having a plurality of strands each of which is formed from a plurality of individual filaments and wherein at least one of said strands contains ones of said texturized filaments, said texturized dental floss substrate having a length, a cross-section perpendicular to said length, an exterior surface, and a depth defined as a distance from said exterior surface toward a center of said cross-section, said texturized dental floss substrate having a substrate weight and an overcoating applied to said exterior surface, said overcoating being formed of a carrier and at least one adjuvant, wherein said overcoating has a weight which exceeds 10% of said substrate weight and wherein said overcoating has a concentration which decreases as said depth increases.

11. The dental floss product of claim 10, said texturized dental floss substrate having an internal region distinct from and bounded by said exterior surface, said dental floss product further comprising a cleaning preparation disposed in spaces between filaments positioned within said internal region, said cleaning preparation have a weight equal to 5% to 120% of said substrate weight.

12. The dental floss product of claim 11, said dental floss product having a total loading weight representing the combination of said weight of said overcoating and said weight of said cleaning preparation, wherein said total loading weight is at least 40 percent of said substrate weight.

13. The dental floss product of claim 11, wherein said at least one of said strands is formed of one of said texturized filaments combined with at least one untexturized filament.

14. The dental floss product of claim 11, wherein said at least one of said strands is formed of only ones of said texturized filaments.

15. The dental floss product of claim 11, wherein said dental floss substrate contains from two to twelve of said strands, and wherein each of said strands contains from 100 to 800 of said individual filaments.

16. The dental floss product of claim 11, wherein said overcoating is formed of an overcoat wax, wherein said overcoat wax is selected from the group consisting of soluble polyethylene glycol, microcrystalline wax, beeswax and paraffin wax, and wherein said at least one overcoat adjuvant is selected from the group consisting of fluoride compounds, anti-microbials, tetrasodium pyrophosphate, peroxides, nitrates, flavorants, flavor enhancers, colorants, antibiotics, plaque inhibitors, polishing agents, fillers and buffering agents.

17. A dental floss product, comprising: a texturized dental floss substrate formed from texturized filaments, said texturized dental floss substrate having a plurality of strands each of which is formed from a plurality of individual filaments and wherein at least one of said strands contains ones of said texturized filaments, said texturized dental floss substrate having a substrate weight, an exterior surface and an internal region distinct from and bounded by said exterior surface, said texturized dental floss substrate having a cleaning preparation disposed in spaces between filaments positioned within said internal region and an overcoating, distinct from said cleaning preparation, applied to said exterior surface, said overcoating being formed of a carrier and at least one adjuvant, wherein said dental floss product has a total loading weight representing the combination of a weight of said overcoating and a weight of said cleaning preparation, said total loading weight being at least 150 percent of said substrate weight.

18. The dental floss product of claim 17, wherein said weight of said cleaning preparation is equal to 5% to 120% of said substrate weight.

19. The dental floss product of claim 18, wherein said at least one of said strands is formed of one of said texturized filaments combined with at least one untexturized filament.

20. The dental floss product of claim 18, wherein said at least one of said strands is formed of only ones of said texturized filaments.

21. The dental floss product of claim 18, wherein said dental floss substrate contains from two to twelve of said strands, and wherein each of said strands contains from 100 to 800 of said individual filaments.

22. The dental floss product of claim 18, wherein said overcoating is formed of an overcoat wax, wherein said overcoat wax is selected from the group consisting of soluble polyethylene glycol, microcrystalline wax, beeswax and paraffin wax, and wherein said at least one overcoat adjuvant is selected from the group consisting of fluoride compounds, antimicrobials, tetrasodium pyrophosphate, peroxides, nitrates, flavorants, flavor enhancers, colorants, antibiotics, plaque inhibitors, polishing agents, fillers and buffering agents.

* * * * *